United States Patent [19]
Oscarsson

[11] Patent Number: 4,657,533
[45] Date of Patent: Apr. 14, 1987

[54] HYPODERMIC INJECTOR DEVICE

[76] Inventor: Rolf A. Oscarsson, 1550 Winchell Dr., Hudson, Ohio 44236

[21] Appl. No.: 857,997

[22] Filed: May 1, 1986

[51] Int. Cl.$^4$ ............................................. A61M 31/00
[52] U.S. Cl. ........................................................ 604/60
[58] Field of Search ....................... 604/48, 51, 57, 59, 604/60-64, 218

[56] References Cited

U.S. PATENT DOCUMENTS

| | | | |
|---|---|---|---|
| 2,502,909 | 4/1950 | Wick et al. | 604/60 |
| 3,016,895 | 1/1962 | Sein | 604/60 |
| 3,744,493 | 7/1973 | Booher et al. | 604/60 |
| 4,451,253 | 5/1984 | Harman | 604/60 |

Primary Examiner—John D. Yasko
Attorney, Agent, or Firm—Body, Vickers, & Daniels

[57] ABSTRACT

A hypodermic injector device for medical injection purposes comprises a one-piece molded plastic member of generally compass-like form having a pair of swing arms hinged together at one end by a hinge loop connector web portion for manual swing movement toward and away from one another. A threaded mounting socket or other type mounting arrangement is provided on the outer end of one of the swing arms for securing thereto, in various use applications of the device, a hollow hypodermic needle or a hypodermic syringe. The other swing arm is formed at its outer end with a thin arcuate push rod portion which, when the swing arms are swung together, is moved through a bore passageway in the mounting socket to effect injections of medicaments or intramuscular implantation of electrodes into a patient through the hollow needle, or injection of the filling from a hypodermic syringe mounted on the device.

29 Claims, 14 Drawing Figures

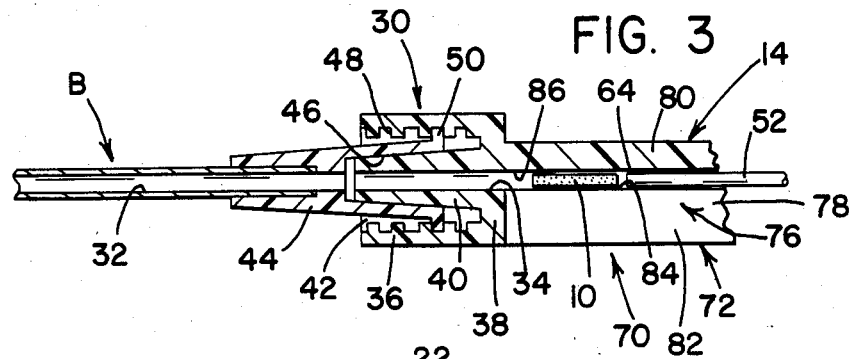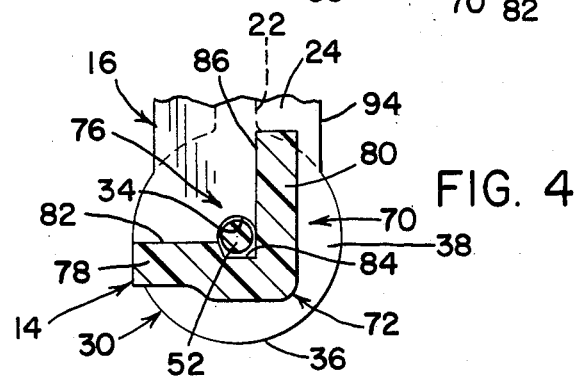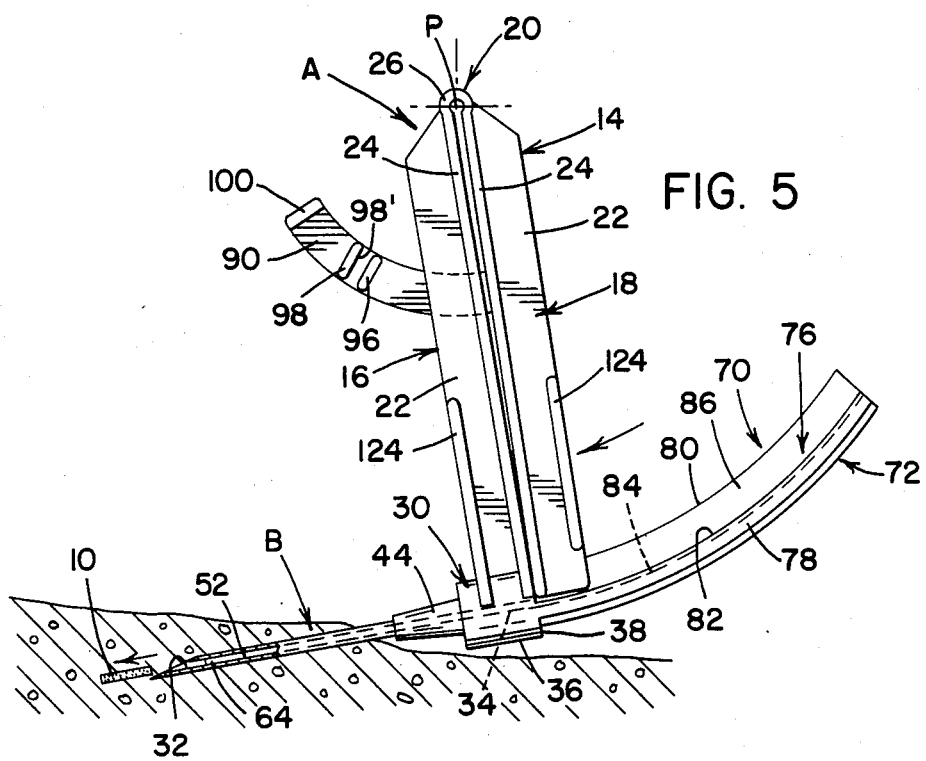

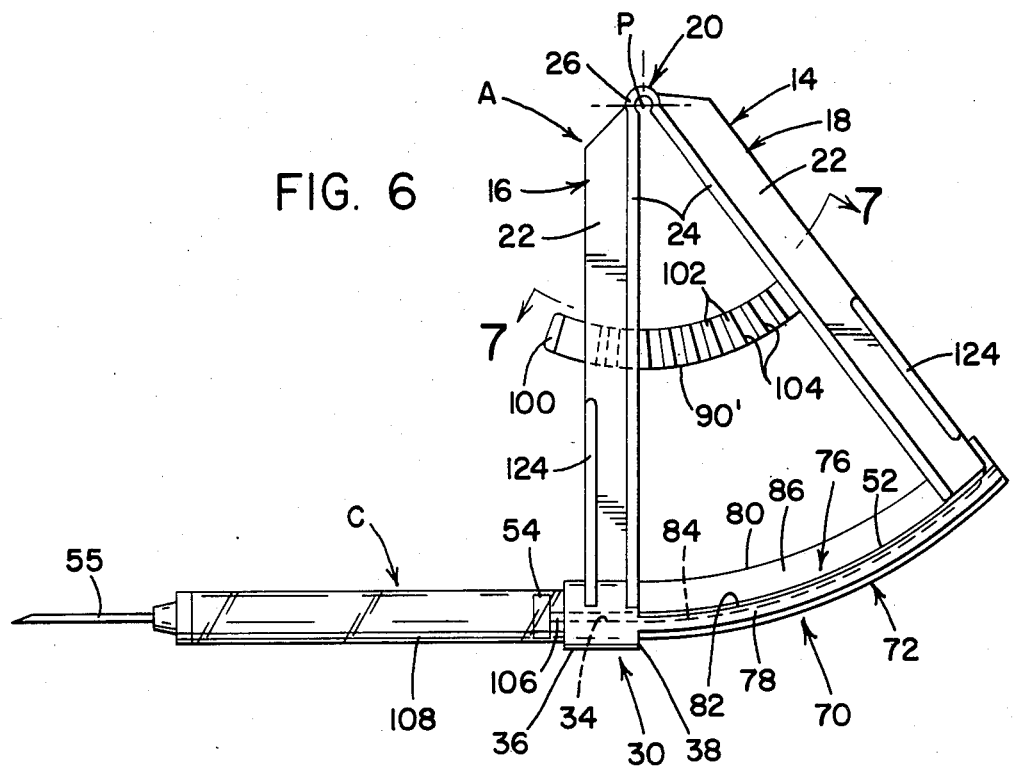
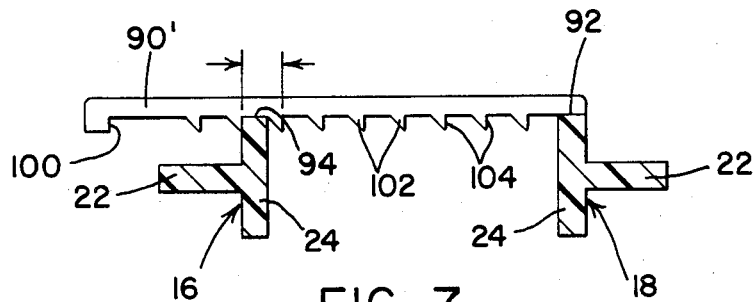
FIG. 6
FIG. 7

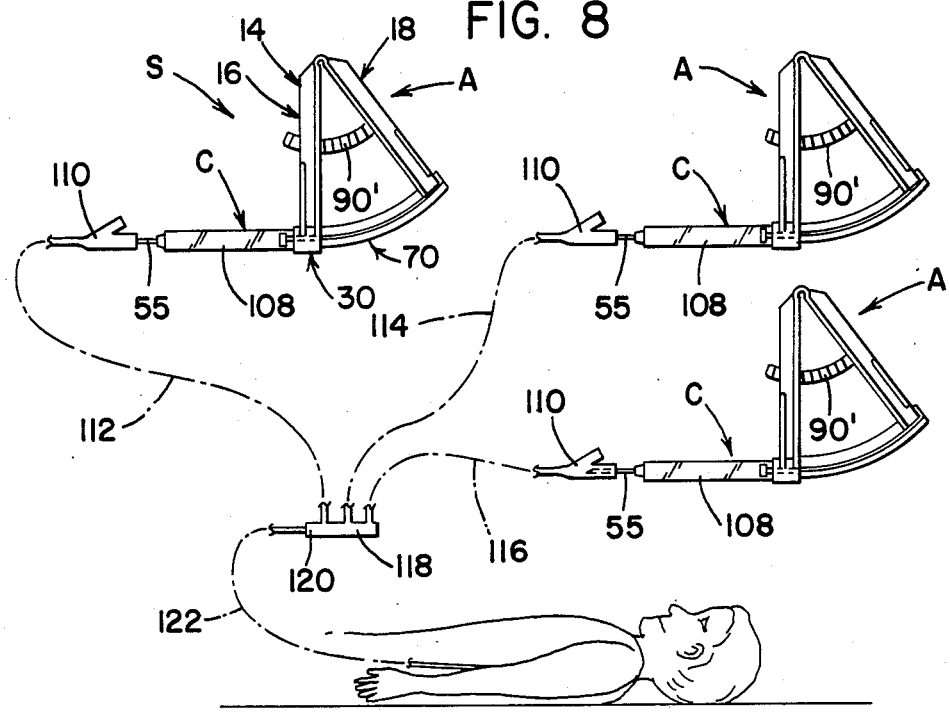
FIG. 8
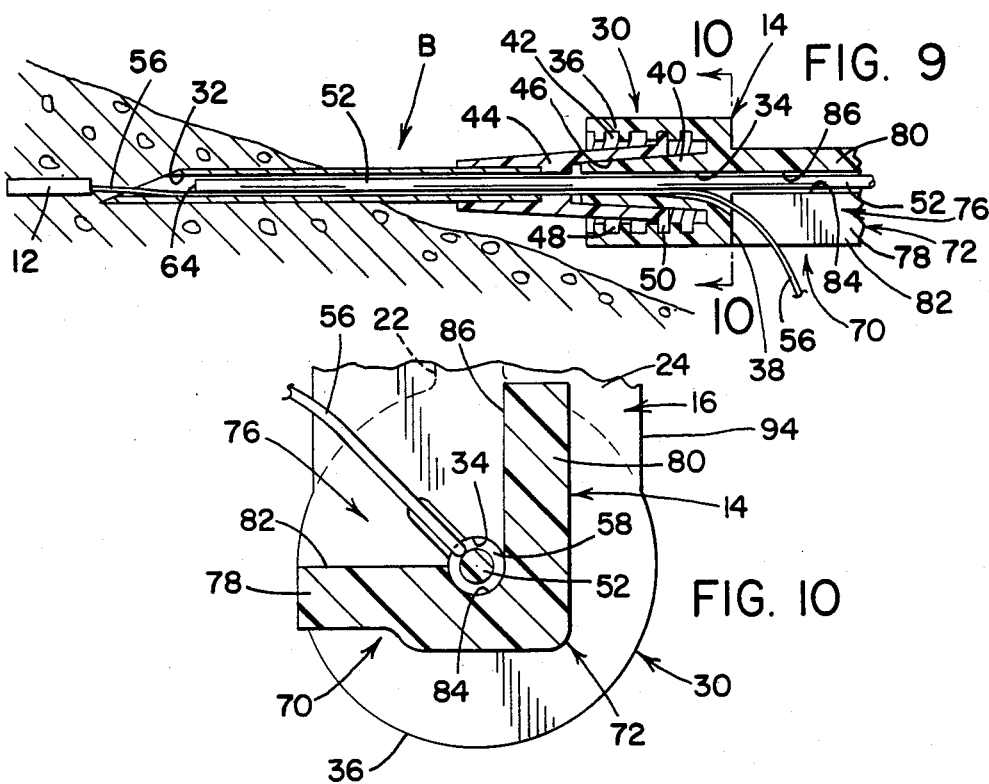
FIG. 9
FIG. 10

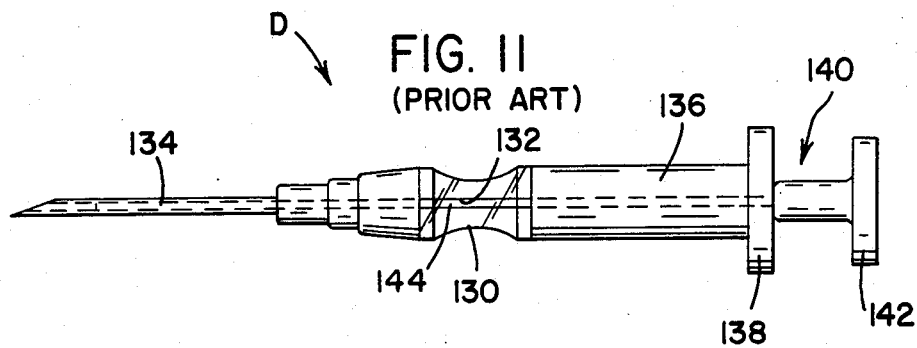
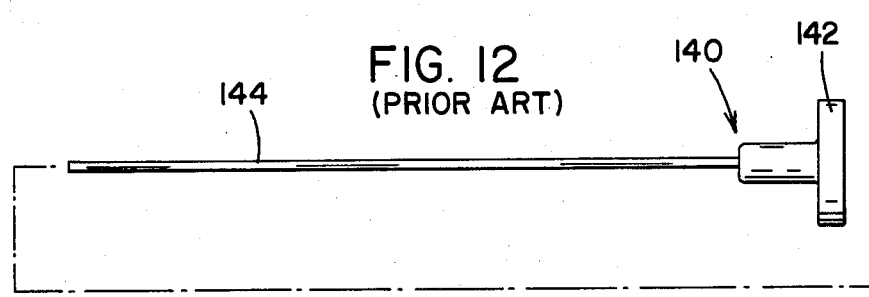
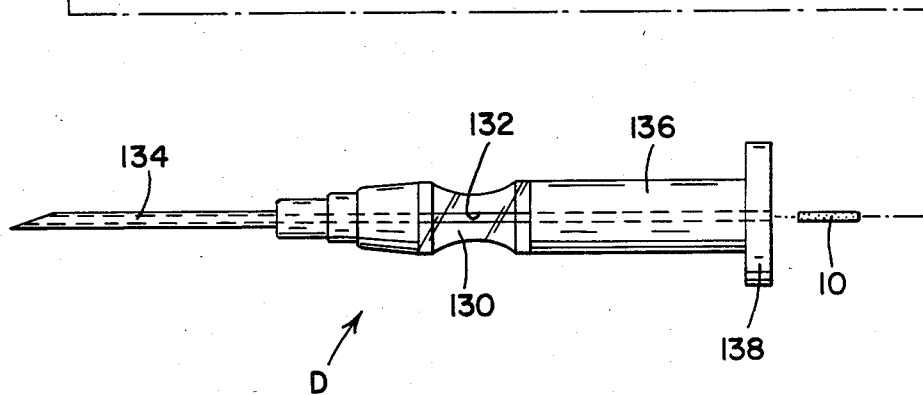

HYPODERMIC INJECTOR DEVICE

The present invention relates, in general, to a hypodermic injector device for effecting hypodermic injections of medicaments or subcutaneous implantations of medicinal pellets or muscle stimulating electrodes into a patient.

BACKGROUND OF THE INVENTION

Heretofore, hypodermic medicinal injections or implantations into a patient frequently have been administered by the use of a hypodermic injector device comprised of a relatively thin barrel member of molded plastic or the like provided with a small diameter passageway through which a cylindrical pellet of a selected medicament may be forced into and through the hollow interior of an implanted hypodermic needle on one end of the barrel member by the thrust of a push rod on a separate plunger member inserted into the other end of the barrel. Both the barrel member and plunger member of such prior hypodermic injector devices are generally comprised of two or more individual component parts which must be separately fabricated and preassembled to form the completed members. As a result, the manufacture of such prior type hypodermic injector devices has been rather time-consuming and comparatively expensive.

In addition, such prior type hypodermic injector devices have been limited in the number of different injection and/or implantation usages for which they are adapted. Thus, they have not been capable of use with conventional hypodermic syringes such as hypodermic injection cartridges containing a predetermined filling of a liquid medicament, to effect the injection of either all, or only selected amounts of, the total medicament in the syringe or cartridge. Nor have such prior type hypodermic injector devices been capable of performing the subcutaneous implantation into a patient of thin electrodes with a trailing electrical conductor wire, such as are commonly employed for muscle stimulation purposes.

SUMMARY OF THE INVENTION

The present invention contemplates a new and improved form of hypodermic injector device which overcomes all of the above referred to problems and others and provides an injector device which not only can be easily and inexpensively fabricated but which also can be employed to perform various different types of conventional hypodermic injection and implantation procedures.

Briefly stated, in accordance with one aspect of the invention a hypodermic injector device is provided comprised of a one-piece molded plastic member of compasslike form having a pair of swing arms hinged together by a hinged connection such as a thin loop-shaped web portion to swing toward and away from each other. One of the swing arms is a support arm provided at its radially outer end with a mounting head provided with mounting means for securing thereto and supporting thereon either a hollow hypodermic needle, or a hypodermic syringe or cartridge provided with such a needle, in a position disposed in the swing plane of the two swing arms and extending from the support arm in a direction approximately perpendicular to the radial extent thereof and oppositely away from the other or actuating swing arm, and with the hollow interior passageway of the hypodermic needle aligned and in communication with a bore passageway extending through the mounting head. The actuating swing arm is formed at its radially outer end with a small diameter flexible push rod extending in cantiliver mounted form therefrom, toward the mounting head on the support swing arm, in an arcuate path centered on the hinge axis of the hinged connection of the two swing arms so as to enter and pass through the bore passageway in the mounting head, on closure swing movement of the swing arms, whereby it may push through the bore passageway and the attached hollow needle a cylindrical medicinal pellet, for example, that is inserted in place in the device in or opposite the entrance end of the bore passageway, thereby to subcutaneously implant the pellet or other medium into the patient through the hollow needle subcutaneously inserted in place in the patient.

According to another aspect of the invention, the support swing arm is formed with a guide member extending from the mounting head on the support swing arm toward the actuator swing arm and provided with a guideway for the push rod extending toward the outer end of the actuator swing arm in an arcuate path centered on the hinge axis of the swing arms to thereby guide the push rod into the bore passageway of the mounting head on closure swing movement of the two swing arms. The guideway for the push rod includes a confining arcuate extending guide groove therein within which the cantilever supported push rod slidably fits and is spring flexed radially outward thereinto, and an upstanding side guide flange against which the actuator swing arm is laterally spring flexed to slidably engage therewith and maintain the push rod slidably seated in the guide groove during the swing closure of the swing arms.

According to still another aspect of the invention, one of the swing arms of the injector device is provided intermediate its ends with a position indicating or setting bar for the swing arms extending from such one swing arm in an arcuate path centered on the pivot axis of the swing arms and in laterally spring flexed engagement against the other one of the spring arms whereby to indicate a selected swing closed position or setting thereof. The arcuate position indicating or setting bar on the one swing arm may be in the form of a ratchet type bar provided with ratchet teeth for engaging with detent means on the other one of the swing arms to retain the swing arms in a selected set swing-closed position, i.e. partially or fully closed position, as where the device is employed to inject into a patient a predetermined dosage amount of the total liquid medicament content of a hypodermic syringe or cartridge mounted on the device.

According to a still further aspect of the invention, the arcuate position-setting bar on the one swing arm is provided adjacent its free end with a stop lug for engaging with the other one of the swing arms to limit separating swing movement of the swing arms and prevent disengagement or separation of the push rod from the guide member.

According to yet another aspect of the invention, a suitable clearance path is provided between the push rod and the wall of the bore passageway in the support swing arm and the wall of the passageway in a hypodermic needle that may be secured onto the device, for the accommodation within such clearance space of a wire conductor from an electrode to be subcutaneously implanted by the device through the hypodermic needle mounted thereon. The clearance path for the electrode wire conductor may be provided, for instance, by a longitudinal groove in the push rod, or by forming the push rod of sufficiently smaller cross-sectional size than the bore passageways in the support swing arm and the hypodermic needle.

The principal object of the invention is to provide a novel hypodermic injector device of simple and inexpensive construction and of universal utility for the performance of a variety of different hypodermic injection and implantation operations.

Another object of the invention is to provide a hypodermic injector device of the above described type which is of one-piece molded plastic light weight construction and which is easy to operate.

Still another object of the invention is to provide a hypodermic injector device which is capable of performing subcutaneous injections of the liquid medicinal fillings of hypodermic syringes or prefilled cartridges, or the subcutaneous implantation of medicinal pellets or electrodes into a patient.

A further object of the invention is to provide a hypodermic injector device of the above described type which can be actuated to and fixed in a selected set position to inject into a patient a selected measured dosage amount of the liquid medicinal filling in a hypodermic syringe or prefilled cartridge.

A still further object of the invention is to provide a hypodermic injector device of the above described type which is capable of subcutaneously implanting an electrically energizable electrode with its trailing wire conductor in an intramuscular position within a patient.

Still another object of the invention is to provide a hypodermic injector device of the above described type which will temporarily lock itself in a preloaded condition, with a medicinal pellet inserted in position therein in readiness for injection into a patient, without the likelihood of the pellet accidentally falling out of and becoming dislodged from the device.

Further objects and advantages of the invention will be apparent from the following detailed description of a preferred species thereof and from the accompanying drawings.

BRIEF DESCRIPTION OF THE DRAWINGS

In the drawings:

FIG. 3 is a fragmentary horizontal sectional view on an enlarged scale of the injector device of FIGS. 1 and 2 shown in its retracted loading position for permitting the insertion thereinto of a cylindrical medicinal injection pellet, as shown;

FIG. 4 is a fragmentary vertical sectional view on an enlarged scale taken on the line 4—4 of FIG. 2;

FIG. 5 is an elevational view on an enlarged scale of the hypodermic injector device comprising the invention shown in subcutaneous implanted position in a patient and in its fully actuated position for effecting the implantation of a medicinal pellet in the patient;

FIG. 6 is an elevational view of a modified form of the hypodermic injector device comprising the invention for injecting into a patient all or a selected measured dosage portion of the medicinal fluid filling in a prefilled hypodermic cartridge mounted on the device;

FIG. 7 is a sectional view taken on the line 7—7 of FIG. 6;

FIG. 8 is a schematic view illustrating a system for intravenously injecting various amounts of differing medicinal fluids into a patient from a plurality of hypodermic injector devices comprising the invention connected through a manifold arrangement to the hypodermic needle inserted in the patients' vein or artery.

FIG. 9 is a fragmentary longitudinal sectional view on an enlarged scale of the hypodermic injector device comprising the invention showing the use thereof to implant a muscle stimulating electrode subcutaneously into a patient;

FIG. 10 is a sectional view on an enlarged scale taken on the line 10—10 of FIG. 9;

FIG. 11 is a side elevation view of a prior art type of hypodermic injector device shown with an attached hypodermic needle; and, FIG. 12 is an exploded view of the prior art injector device shown in FIG. 11 along with a medicinal pellet for insertion thereinto.

DESCRIPTION OF THE PREFERRED EMBODIMENT

Figure 1:
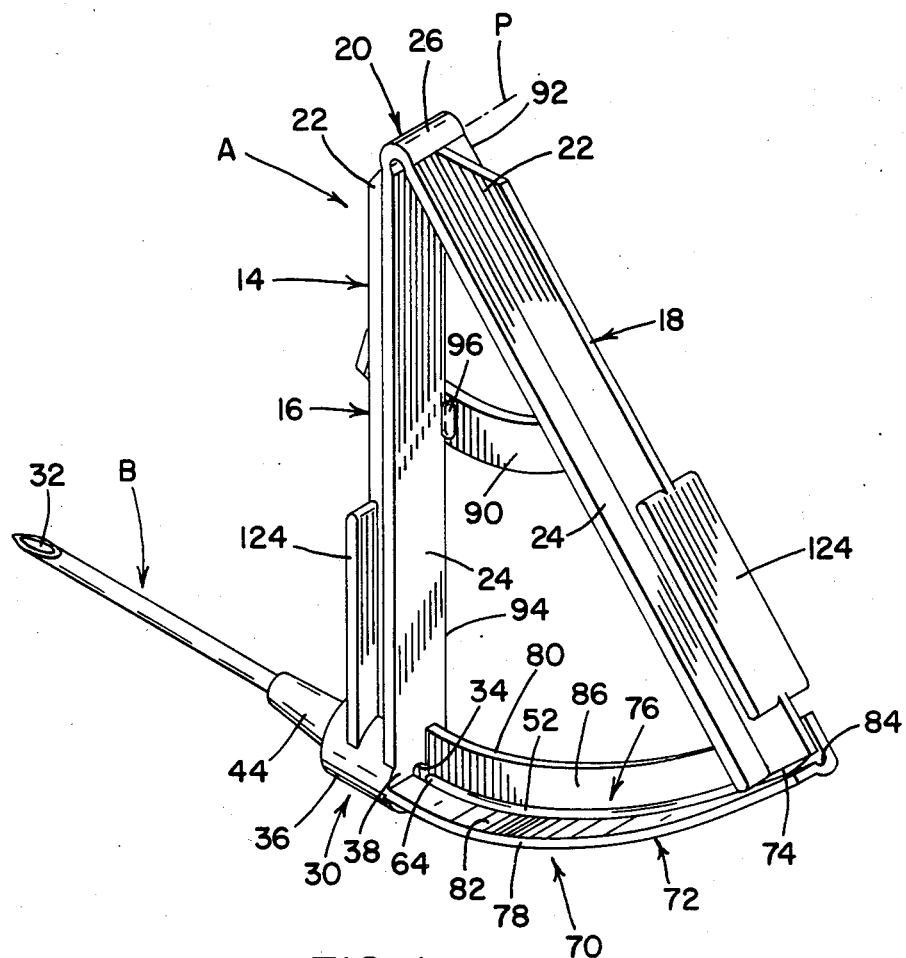
FIG. 1 is a perspective view on an enlarged scale of a hypodermic injector device comprising the invention shown in its normal position in readiness for actuation to effect a hypodermic injection or implantation operation.
Figure 2:
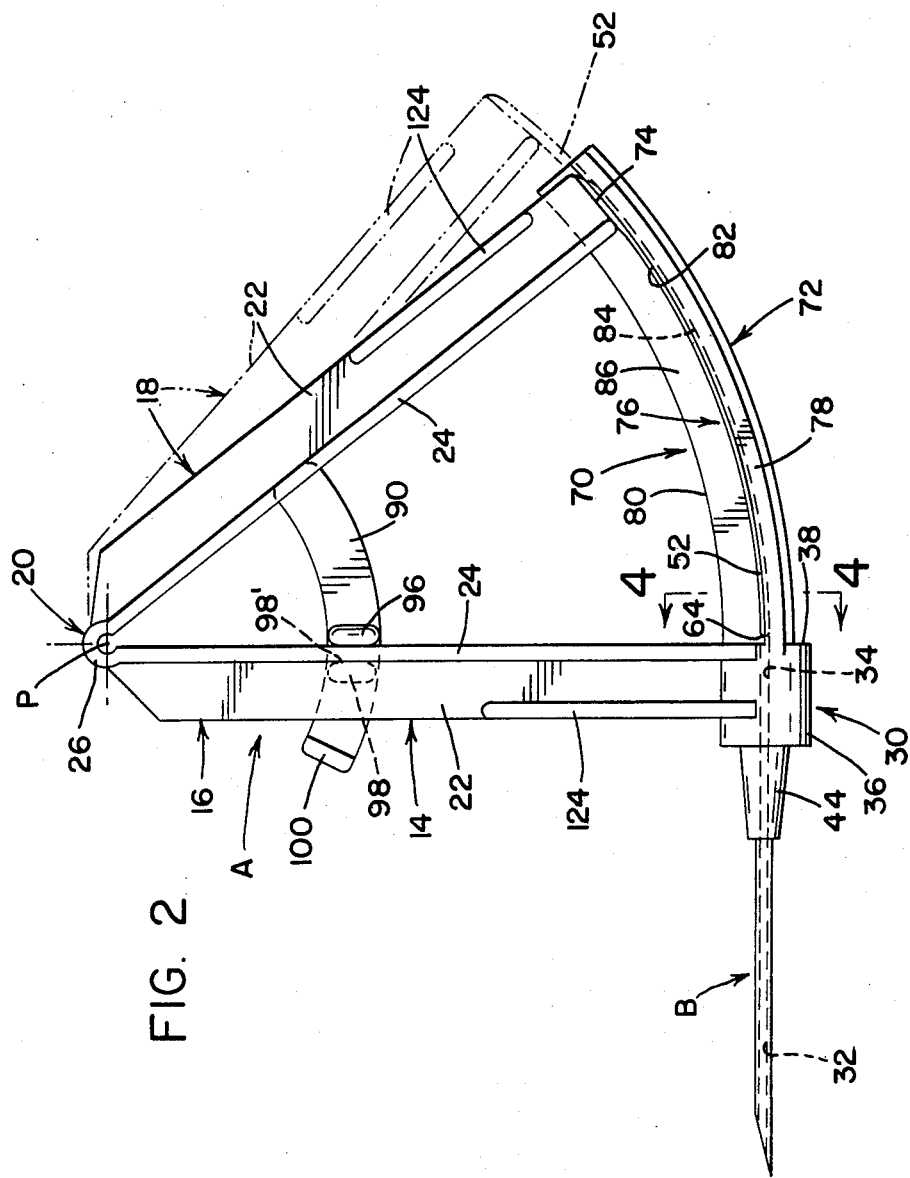
FIG. 2 is an elevational view on an enlarged scale of the injector device shown in FIG. 1.

Referring now to the drawings wherein the showings are for the purpose of illustrating a preferred embodiment of the invention only and not for the purpose of limiting same, the figures show a hypodermic injector device A adapted for mounting thereon of either a conventional hollow hypodermic needle B as shown in FIGS. 1-3, or a hypodermic syringe or prefilled hypodermic cartridge C containing a filling of a medical fluid, as shown in FIGS. 6 and 8. The injector device A may be utilized for a variety of different conventional hypodermic injection purposes. Thus, when equipped with a hollow hypodermic needle B, the device A may be employed to implant into a patient either a thin cylindrical medicinal pellet 10 as shown in FIG. 5 or a muscle stimulating electrode 12 as shown in FIG. 9. The device may be also employed for intravenous injections of medicinal fluids into a patient from a hypodermic syringe or a prefilled hypodermic cartridge C mounted on the device, as shown in FIG. 6.

The hypodermic injector device A according to the invention comprises a one-piece molded plastic member 14 formed of a suitable indurated plastic material and of generally compass-like form having a pair of swing arms comprising a support swing arm 16 and an actuator swing arm 18 hinged together at one end by a hinged connection 20 and extending radially outward therefrom at an acute angle to one another for swing movement toward and away from each other about the pivot axis P of their hinged connection 20. The swing arms 16, 18 preferably are of T-shaped cross-section (FIG. 7) with a central rib portion 22 extending along a cross-flange portion 24, and they are joined together at one end by a thin loop-shaped flexible web portion 26 forming a continuation of and interconnecting the flange portions 24 of the respective swing arms 16 and 18.

The support swing arm 16 is provided at its radially outward end with a mounting head 30 for securing thereto a hypodermic needle B, or a hypodermic syringe or prefilled cartridge C, in a position thereon extending in a direction away from the actuator swing arm 18, with the bore passage 32 of the needle B or the axis of the cartridge C axially aligned with a bore passageway 34 which extends through the mounting head 30 in a direction approximately normal to the radial extent of the support swing arm 16 and is disposed substantially in the swing plane of the two support arms 16, 18. For such purpose, the mounting head 30 is formed with suitable mounting means including an outer sleeve portion 36 closed at one end by an end closure wall 38 and extending therefrom in a direction away from the actuator arm 18 and axially aligned with the bore passageway 34 in the mounting head. Internally of the sleeve portion 36, the mounting head is formed with a slightly conical mounting post portion 40 extending from the end closure wall 38 through the sleeve portion in spaced relation to the inner wall thereof and axially aligned with the bore passageway 34 which extends through the mounting post portion 40. The mounting post portion 40 thus is enclosed within the sleeve portion 36 to form therewith an annular chamber 42 for the accommodation therein of the mounting end 44 of the hypodermic needle B or cartridge C. As shown in FIG. 3, the conical mounting post 40 in the mounting head 30 is adapted to fit tightly into the correspondingly tapered mounting socket 46 in the mounting end 44 of the hypodermic needle B or cartridge C so as to firmly support the latter in axially aligned position on the mounting post portion 40. The inner wall of the sleeve portion 36 of the mounting head 30 may be formed with a screw thread 48 for threaded engagement with a suitable screw thread means 50 on the mounting end 44 of the hypodermic needle B or cartridge C to thereby tightly seat the conical mounting socket 46 thereof onto the mounting post 40 of the mounting head 30 and align the bore passage 32 of the needle with the bore passageway 34 in the mounting head.

The actuator swing arm 18 is formed at its radially outward end with an integral flexible push rod element 52 which extends in cantilever supported fashion therefrom in an arcuate path centered on the pivot axis P of the swing arms 16, 18 and in a direction toward the mounting head 30 on the swing arm 16 for insertion into and passage through the bore passageway 34 in the mounting head 30 on closure swing movement of the swing arms 16, 18. The actuated push rod 52 thereby either forces the medicinal pellet 10 or the electrode 12 through the bore passageway 34 and the hollow needle B so as to implant one or the other subcutaneously into a patient as shown in FIGS. 5 and 9, or actuates the plunger 54 of the hypodermic syringe or a prefilled hypodermic cartridge C mounted on the injector device so as to subcutaneously or intravenously inject into a patient, through the hypodermic needle 55 normally provided on such syringes or cartridges, the medical fluid contained therein. For this purpose, the push rod 52 is formed of small enough cross-sectional size, e.g., of a diameter slightly smaller than that of the bore passageway 34 in the mounting head 30 and the bore passage 32 of the hypodermic needle B mounted thereon, to permit the free and easy movement of the push rod into the bore passageway 34 and therethrough on closure swing movement of the swing arms 16, 18.

Figure 10A:
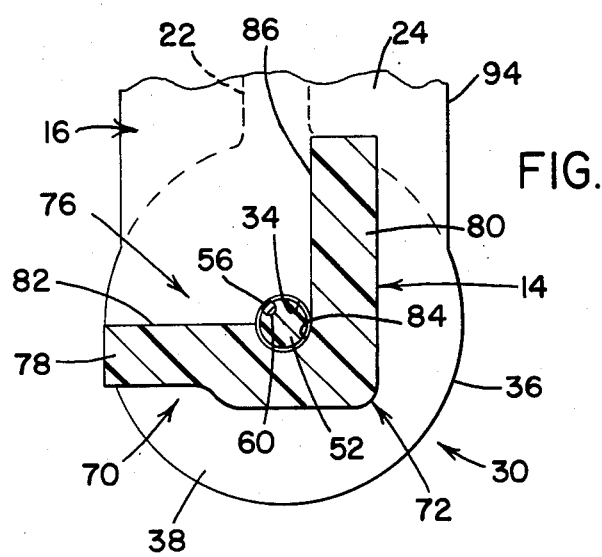
FIGS. 10A and 10B are fragmentary vertical sectional views similar to FIG. 4 of two different modified forms of the injection device.
Figure 10B:
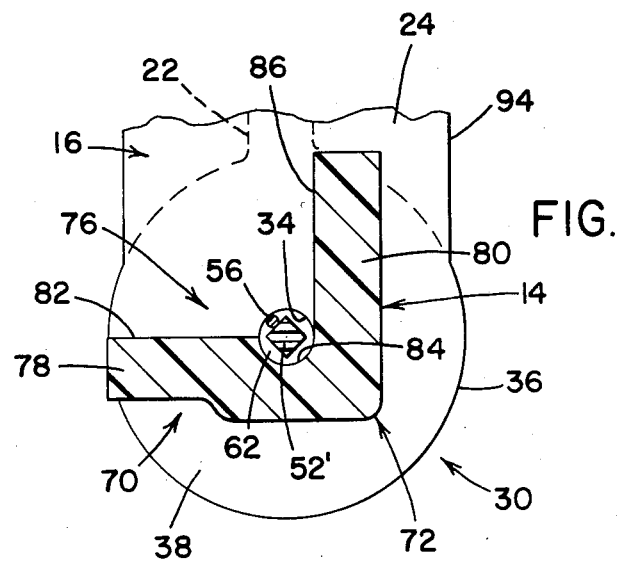

To enable the use of the injector device A, however, for the intramuscular implantation into a patient, for muscle stimulation purposes, of an electrically energizable electrode 12 having a trailing wire conductor 56 as shown in FIG. 9, it is necessary that sufficient clearance space be provided between the push rod 52 and the inside wall surfaces of both the bore passageway 34 in the mounting head 30 and the bore passage 32 of the hypodermic needle B in order to thereby prevent any binding of the wire conductor 56 therebetween, on extraction of the hypodermic needle from the patient, such as might result in the undesired added extraction or pulling of the implanted electrode out from the patient along with the needle B. To this end, therefore, the push rod 52 may be formed of cylindrical cross-section, as shown in FIG. 10, with a diameter sufficiently smaller than that of the bore passageway 34 to provide the necessary annular clearance space 58 between the push rod 52 and the wall of the bore passageway 34 to freely accommodate the wire conductor 56 therein and prevent the binding therebetween of the electrode wire conductor 56 on extraction of the hypodermic needle B from the patient and pulling thereof off the outer end of the wire conductor 56. Alternatively for such purpose and as shown in FIG. 10A, the push rod 52 may be formed of circular cross-sectional shape almost as large in diameter, for strength purposes, as that of the bore passage 34 in the mounting head 30 but provided with a longitudinal slot or groove 60 to provide the necessary clearance space for the accommodation therein of the electrode wire conductor 56. According to another modification of the invention for this purpose and as shown in FIG. 10B, the push rod 52' may be formed of a cross-sectional shape other than the circular cross-sectional shape of the bore passageway 34, e.g., it may be of rectangular or square shape as shown, to provide the necessary clearance space 62 between the push rod 52' and the wall of both the bore passageway 34 and the bore passage 32 of the needle B, for the accommodation therein of the electrode wire conductor 56.

To guide the free or nose end 64 of the push rod 52 into the entrance end of the bore passageway 34 in the mounting head 30, on closure swing movement of the two swing arms 16 and 18, the support swing arm 16 is formed with guide means 70 comprising a guide member 72 extending from the mounting head 30 on the outer end of the swing arm 16 in cantilever supported fashion therefrom, toward the radially outward end 74 of the actuator swing arm 18 in an arcuate path centered on the pivot axis P of the hinged connection 20 of the two swing arms 16, 18 and provided with a corresponding arcuate extending guideway 76 for the push rod 52. The guide member 72 is of L-shaped cross-section, as best shown in FIGS. 4 and 10, and comprises an arcuate base flange guideway portion 78 extending in a cylindrical manner about the pivot axis P of the hinged connection 20 of the two swing arms 16, 18, and an arcuate side guide flange portion 80 extending along the rear side edge of the arcuate extent of the base flange portion 78 and radially inwardly of the swing arms 16, 18 and disposed in a plane parallel to the plane of swing movement of the swing arms 16, 18. As shown in FIGS. 4 and 10, the base flange portion 78 of the guide member 72 is located slightly radially outward of the bore passageway 34 in the mounting head 30, with its radially inward facing arcuate side 82 more or less aligned with the axis of the bore passageway 34 at the entrance end thereof.

The arcuate guideway 76 formed by the guide member 72 includes a corresponding arcuate extending guide groove 84 formed in the radially inward facing arcuate side 82 of the base flange portion 78 of the guide member, within which groove 84 the arcuate extending push rod 52 on the actuating arm 18 fits, in the rest or opened position of the swing arms 16, 18, and arcuately slides on swing movement of the swing arms, to thereby guide the nose end 64 of the push rod into the entrance end of the bore passageway 34 in the mounting head 30. As shown in FIGS. 4 and 10, the guide groove 84 extends immediately alongside the front side 86 of the side guide flange portion 80 of the guide member 72. The guide groove 84 is of suitable cross-sectional shape to properly confine the push rod 52 therein and guide it into the entrance end of the bore passageway 34 in the mounting head 30 on closure swing movement of the swing arms 16, 18. Thus, where the push rod 52 is in the form of an arcuately curved thin cylindrical member as shown in FIGS. 4 and 10, the guide groove 84 in such case may then be of either channel shape (FIG. 4) or of semi-circular cross-section (FIG. 10) and axially aligned with the bore passageway 34, with a cross-sectional size or diameter approximately corresponding to but no greater than the diameter of the bore passageway 34 so as not to present an annular shoulder at the entrance end thereof against which the push rod would be apt to abut and catch and thus prevent the free sliding movement thereof into the bore passageway 34 on closure swing movement of the swing arms 16, 18.

The cantilever supported push rod 52 is spring flexed or biased radially outward against the guide member 72 and into the guide groove 84 in order to thereby maintain the push rod positively seated therein against undesired dislodgement therefrom during the use of the device A. For this purpose also, the actuator swing arm 18 is laterally spring flexed or biased against the front side face 86 of the side guide flange portion 80 of the guide member 72 in order to also maintain the push rod biased against the face 86 and slidably seated in the guide groove 84 at all times against dislodgement therefrom.

One of the swing arms 16 or 18, preferably the actuator swing arm 18 as shown, is formed intermediate its opposite ends with a flat, position-setting or indicator bar 90 extending in cantilever mounted fashion therefrom toward the other one of the swing arms in an arcuate path centered on the pivot axis P of the swing arms, and it is disposed in a plane parallel to the plane of swing movement thereof. The arcuate bar 90 extends from the rear side edge 92 of the flange portion 24 on the one swing arm, e.g., swing arm 18, in a flatwise position extending across the rear side edge 94 of the other swing arm, e.g., swing arm 16 and it is held in laterally spring flexed sliding engagement therewith by the laterally spring flexed swing arm 18.

The arcuate position-setting bar 90 may be provided with a closely spaced pair of position-setting ribs 96 and 98 (FIGS. 1, 2 and 5) extending transversely across the flat front side of the bar 90 and between which the flange portion 24 of the support swing arm 16 is adapted to snap-lock, on swing closure of the swing arms 16, 18, to thereby locate and set the spring arms in a predetermined partially swing closed position, as shown in FIG. 2. Thus, the position-setting ribs 96, 98 may be employed to set the swing arms 16, 18 in that partial swing closed position thereof as shown in FIGS. 1 and 2 wherein the nose end 64 of the push rod 62 is located immediately outwardly adjacent the entrance end of the bore passageway 34 in the mounting head 30 of the device A in order to thereby hold and retain in preloaded position within the bore passageway 34 of the device A, and prevent the dislodgement therefrom and from the guide groove 84, of a medicinal pellet 10 placed in the guide groove and pushed by the push rod 52 into the entrance end of the bore passageway 34 (FIG. 3). The swing arms 16, 18, however, are normally held by the spring closure force of their loop-shaped flexible connecting web portion 26 in a retracted position wherein the nose end 64 of the push rod 52 is spaced from the entrance end of the bore passageway 34 a sufficient distance to enable the insertion therebetween, and placement in the guide groove 84, of the individual medicinal pellets 10 to be implanted by the device A. The position-setting ribs 96, 98 are preferably of rounded transverse cross-sectional shape to permit them to ride easily over the rear side edge 94 of the flange portion 24 of swing arm 16 during the swing closure of the swing arms 16, 18. The inner side face 98' (FIG. 5) of the forwardmost one 98 of the two position-setting ribs 96, 98, however, is preferably formed perpendicular to the front face of the arcuate bar 90, rather than being of rounded form, in order to thereby provide a square or positive stop shoulder serving to lock the swing arms 16, 18 in their partially swing closed or pellet preloaded position against undesired accidental swing opening thereof such as would permit possible dislodgement of the medicinal pellet 10 from the retaining guide groove 84 therefor. The arcuate bar 90 is also provided at its free end with a stop lug 100 projecting from the front side of the bar 90 and adapted to normally abut against the flange portion 24 of the support swing arm 16, on opening swing movement of the swing arms 16, 18, to thereby limit separating swing movement of the swing arms and prevent the disengagement of the push rod 52 endwise off the free end of the guide member 72.

In the modified form of hypodermic injector device shown in FIGS. 6 and 7 for injecting medical fluid from a hypodermic syringe or prefilled cartridge C into a patient, a modified type arcuate position-setting or indicator bar is provided on the device A in the form of a ratchet bar 90' having a plurality of ratchet teeth 102 spaced therealong with square or perpendicular locking or stop faces 104 projecting from the front side of the bar 90', for snap-locking over the side edge 94 of the flange 24 on the support swing arm 16 to set and maintain the swing arms 16, 18 in a selected swing closed position and thereby limit the amount of medicinal fluid injected by the device into a patient from a hypodermic syringe or prefilled cartridge C mounted on the device A. On swing closure of the swing arms 16, 18 the nose end 64 of the push rod 52 engages endwise against the outer end of the piston rod 106 which is connected to and operates the plunger 54 of the syringe or cartridge C and which extends back through the bore passageway 34 and into the guide groove 84 in the guide member 72 of the device A. The push rod 52 thus drives the plunger 54 forwardly through the fluid filled barrel 108 of the syringe or cartridge C to force a portion of or all the medicinal fluid contained therein, depending on the extent of swing closure movement of the swing arms 16, 18, through the hypodermic needle 55 on the discharge end of the barrel 108 and into the patient in which the needle 55 is inserted. The spacing of the stop faces 104 on the ratchet teeth 102 of the arcuate position-setting bar 90' may be graduated in even spacings to indicate desired uniform injected amounts of the medicinal fluid, e.g., of 1cc or a fraction of 1cc, for each of the ratchet teeth graduations or spacings.

FIG. 8 illustrates a system S which may be utilized by an anesthesiologist, for instance, to intravenously inject different medicinal drugs at prescribed time intervals into a patient from a plurality of hypodermic syringes or prefilled cartridges C mounted on respective ones of a plurality (three in the particular case illustrated) of hypodermic injector devices A according to FIGS. 6 and 7. In the system illustrated in FIG. 8, the hypodermic needles 55 of the individual syringes or cartridges C mounted on the various injector devices A are each connected, through separate conventional saline solution continuous flow units 110 and separate flexible plastic tubing sections 112, 114, 116, into a manifold member 118 having a single outlet 120 which is connected by a flexible plastic tube 122 to a hypodermic needle (not shown) intravenously inserted into the patient. With the system S, therefor, prescribed dosage amounts of the different medicinal fluids in the individual syringes or cartridges C, as denoted by the dosage indicating graduations or ratchet teeth 102 on the arcuate ratchet bars 90', then can be injected into the patient from time-to-time simply by the required degree of swing closure movement of the swing arms 16, 18 of respective ones of the injector devices.

As best shown in FIG. 1, the swing arms 16, 18 of the injector device A are each formed, adjacent their radially outward ends, with a flat pad portion 124 flush with the outer side edge of, and extending to either side of the rib portion 22 of the respective swing arm 16 or 18. The pad portions 124 provide convenient finger grips on the swing arms 16, 18 for an operator to grasp them in one hand and swing close them so as to actuate the injector device A.

From the above description, it will be evident that a hypodermic injector device A is provided which is of simple RM-7331 and easily fabricated, inexpensive light weight construction and of universal service application, and comprised of only a single molded plastic member as compared to prior art devices such as, for example, the device D shown in FIGS. 11 and 12 which is comprised of a number of individual component parts that must be separately manufactured and then assembled to form the completed injector device D. The illustrated prior art injector device D includes a molded clear plastic finger grippable barrel member 130 of anticlastic shape and an axial bore passageway 132 therethrough and cylindrical ends for fitting thereonto a hypodermic needle 134 on one end and a molded plastic end cap sleeve 136 on the other end having a flanged end 138 and an axially aligned bore passageway therethrough. The prior art device D further includes a separate plunger assembly 140 comprised of a molded finger grip button 142 secured on one end of an elongated metal push pin 144 the other end of which is adapted for insertion into and passage through the bore passageway of the barrel member 130 to push therethrough and out of the hollow needle 134 a cylindrical medicinal pellet 10 previously inserted into the entrance end of the bore passageway in the end cap sleeve 136. Besides their being of expensive multi-component construction, such prior art injector devices D also are disadvantageous because of their limited usage only for the implantation of medicinal pellets into a patient. They do not have the desirable universal application usage feature possessed by the hypodermic injector device A according to the invention for also injecting liquid medicaments from a hypodermic syringe or cartridge into a patient or subcutaneously implanting into a patient a thin electrode with a trailing electrical conductor wire such as is commonly employed for muscle stimulation purposes.

The invention has been described in connection with a preferred embodiment thereof. Obviously, modifications and alterations will occur to others upon a reading and understanding of this specification and it is my intention to include such modifications and alterations insofar as they come within the scope of the appended claims.

Having thus described the invention, it is claimed:
1. A hypodermic injector device comprising a molded plastic member of generally compass like form having a pair of swing arms comprising a support arm and an actuator arm hinged together at one end by a hinged connection and extending radially outward therefrom at an acuate angle to one another for swing movement toward and away from each other, mounting means on the outer end of said support swing arm for securing thereto a hollow hypodermic needle assembly with its needle passageway aligned with an essentially matching diameter bore passageway formed in the outer end of said support swing arm and disposed in the plane of swing movement of said swing arms and extending normal to the radial extent of said support swing arm, and a flexible push rod on the outer end of said actuator swing arm extending in an arcuate path toward the outer end of said support arm and of smaller cross-sectional size than said bore passageway for insertion thereinto and passage therethrough on swing closure of said swing arms.

2. An injector device as defined in claim 1, and including guide means on said support arm for guiding the said push rod into said bore passageway on swing closure of said swing arms.

3. An injector device as defined in claim 2, wherein the said guide means comprises a guide member extending from the outer end of said support swing arm in a direction toward said actuator swing arm and provided with an arcuate guideway for said push rod centered on the hinge axis of said hinged connection.

4. An injector device as defined in claim 3, wherein the said arcuate guideway includes an arcuate guide groove in the radially inward face of said guide member within which the said push rod slidably fits and is spring flexed radially outward thereinto to guide it into the said bore passageway on swing closure of said swing arms.

5. An injector device as defined in claim 1, wherein the said hinged connection of said swing arms is constituted by a thin loop-shaped interconnecting flexible web portion of said molded member.

6. An injector device as defined in claim 2, wherein the said hinged connection of said swing arms is constituted by a thin loop-shaped interconnecting flexible web portion of said molded member.

7. An injector device as defined in claim 3, wherein the said hinged connection of said swing arms is constituted by a thin loop-shaped interconnecting flexible web portion of said molded member normally holding the said actuator swing arm in a loaded position with the free end of said push rod located adjacent the entrance end of said bore passageway.

8. An injector device as defined in claim 4, wherein the said hinged connection of said swing arms is constituted by a thin loop-shaped interconnecting flexible web portion of said molded member normally holding the said actuator swing arm in a loaded position with the free end of said push rod located adjacent the entrance end of said bore passageway.

9. An injector device as defined in claim 4, wherein the said arcuate guideway of said guide member includes a corresponding arcuate side guide flange portion thereon extending radially inward of said swing arms in a plane parallel to the plane of swing movement thereof, and the said guide groove in said guide member extends immediately alongside said side guide flange, the said outer end of said actuator swing arm along with its said flexible push rod being laterally spring flexed against the side guide flange so as to slidably engage therewith and maintain the push rod slidably seated in said guide groove during the swing closure of said swing arms.

10. An injector device as defined in claim 3, wherein the said guide member is of arcuate form and of L-shaped cross-section and is comprised of an arcuate base flange guideway portion extending in a cylindrical manner about the pivot axis of said hinged connection and an arcuate side guide flange portion extending inwardly of the device from said base flange portion toward the said hinged connection and disposed in a plane parallel to the plane of swing movement of said swing arms.

11. An injector device as defined in claim 10, wherein the said guideway includes an arcuate guide groove in the radially inward face of said base flange portion within which the said push rod slidably fits and is spring flexed radially outward thereinto to guide it into the said bore passageway.

12. An injector device as defined in claim 11, wherein the said guide groove in said base flange portion extends immediately alongside said side guide flange portion of said guide member, and the said actuator swing arm is laterally spring flexed to urge the outer end thereof and the push rod thereon against the said side guide flange and maintain the push rod slidably seated in said guide groove during the swing closure of said swing arms.

13. An injector device as defined in claim 4, wherein the said mounting means on said support swing arm comprises a slightly conical mounting post portion extending therefrom in a direction opposite to the said guide member and through which post portion the said bore passageway extends axially, and an outer sleeve portion axially surrounding said post portion in spaced relation thereto and having an open end at the outer end of said post, said sleeve being internally threaded for screw-threaded engagement with the mounting end of a hypodermic needle.

14. An injector device as defined in claim 1, wherein one of said swing arms is provided with a laterally flexible arcuate position-setting bar for the swing arms, said arcuate bar being centered on the pivot axis of said hinged connection and maintained in laterally spring flexed engagement with the other one of said swing arms.

15. An injector device as defined in claim 14, wherein the said arcuate position-setting bar is formed on the said actuator swing arm.

16. An injector device as defined in claim 14, wherein the said arcuate position-setting bar is provided with ratchet teeth spaced apart along the arcuate extent thereof and engageable with detent means on the other one of said swing arms to maintain the two swing arms in a selected relative swing closed position.

17. An injector device as defined in claim 16, wherein the said detent means is constituted by a flange on said other one of said swing arms extending along the radial length thereof.

18. An injector device as defined in claim 14, wherein the said arcuate position-setting bar is provided adjacent its free end with a stop lug projecting from that side of the bar engaged with the said other one of said swing arms so as to normally abut thereagainst to limit separating swinging movement of said swing arms and prevent disengagement of said push rod from said guide member.

19. An injector device as defined in claim 1, wherein a clearance path is provided between the said push rod and the wall of the said bore passageway in said support swing arm for the accommodation therebetween of a wire conductor from an electrode to be subcutaneously implanted by the device through said hollow hypodermic needle.

20. An injector device as defined in claim 19, wherein the said push rod is formed with a longitudinally extending groove to provide the said clearance path for the wire conductor from the electrode.

21. An injector device as defined in claim 1, wherein the said swing arms are of T-shaped cross-section, with a central rib portion extending along a cross flange portion, and are joined together by the said hinged connection with their said flange portions facing one another, and the said hinged connection is constituted by a thin loop-shaped web portion interconnecting and forming a continuation of the said flange portions of said swing arms.

22. An injector device as defined in claim 21, wherein the said swing arms are each provided with a flat surface grip pad portion extending along at least a portion of the length of the outer edge of the said rib portion on the respective swing arm adjacent the outer end thereof, with the plane of said flat pad disposed parallel to the plane of the said flange portion of the respective swing arm.

23. A hypodermic injector device comprising a one-piece molded plastic member of generally compass-like form having a pair of swing arms hinged together at one end by a hinge connection and extending radially outward therefrom at an acute angle to one another for swing movement toward and away from each other in their common plane, one of said swing arms being a support arm and the other one an actuator arm, said support arm being provided with a guide member extending from its radially outer end toward the radially outer end of said actuator swing arm and provided with an arcuate guideway centered on the pivot axis of said hinged connection and with which guideway the said outer end of said actuator swing arm is in sliding engagement arcuately around said pivot axis, a mounting head on the said outer end of said support swing arm and having a small diameter bore passageway therethrough disposed approximately in the plane of said swing arms and extending approximately normal to the radial extent of said support swing arm and located thereon radially inward of the said arcuate guideway of said guide member, said mounting head being provided with mounting means for securing thereto a hollow hypodermic needle assembly with its tubular passageway aligned with the said bore passageway in said mounting head, and said actuator swing arm being provided at its outer end with a flexible push rod of smaller cross-sectional size than said bore passageway and extending toward the mounting head on said support swing arm, said push rod being of arcuate lengthwise shape matching said arcuate guideway and spring flexed radially outward thereagainst so as to be guided thereby into the said bore passageway in said mounting head on swing closure of said swing arms.

24. An injector device as defined in claim 23, wherein the said arcuate guideway is provided with a corresponding arcuate guide groove extending therealong within which the said flexible push rod is slidably received to guide it into the said bore passageway in said mounting head on swing closure of said swing arms 25. An injector device as defined in claim 23, wherein the said hinged connection of said swing arms is constituted by a thin loop-shaped interconnecting web portion of said molded member.

26. An injector device as defined in claim 24, wherein the said hinged connection of said swing arms is constituted by a thin loop-shaped interconnecting web portion of said molded member.

27. An injector device as defined in claim 23, wherein the said mounting means on said mounting head comprises a slightly conical mounting post portion through which the said bore passageway extends axially, and an outer sleeve portion axially surrounding said post portion in spaced relation thereto and internally threaded for screw threaded engagement with the mounting end of a hypodermic needle.

28. An injector device as defined in claim 24, wherein the said arcuate guideway of said guide member includes a corresponding arcuate side guide flange portion thereon extending radially inward of said swing arms in a plane parallel to the plane of swing movement thereof, and the said guide groove in said guide member extends immediately alongside said side guide flange, the said outer end of said actuator swing arm along with its said flexible push rod being laterally spring flexed against the said side guide flange so as to slidably engage therewith and maintain the push rod slidably seated in said guide groove during the swing closure of said swing arms.

29. An injector device as defined in claim 14, wherein the said arcuate piston-setting bar is provided with a pair of rounded position-setting projections spaced apart along the arcuate extent thereof and between which detent means on the other one of said swing arms is engageable to set the two swing arms in a partially swing-closed position thereof with the nose end of said push rod located immediately outwardly adjacent the entrance end of said bore passageway so as to thereby hold and maintain in preloaded inserted position within said bore passageway a medicinal pellet pushed thereinto by the push rod.

* * * * *